(12) United States Patent
Feucht et al.

(10) Patent No.: US 7,468,608 B2
(45) Date of Patent: Dec. 23, 2008

(54) DEVICE AND METHOD FOR DETECTING A SUBSTANCE OF A LIQUID

(75) Inventors: Hans-Dieter Feucht, Renningen (DE); Reinhard Gabl, Munich (DE); Wolfram Wersing, Bergen (DE); Heinrich Zeininger, Obermichelbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/521,736

(22) PCT Filed: Jul. 3, 2003

(86) PCT No.: PCT/DE03/02226

§ 371 (c)(1),
(2), (4) Date: Sep. 21, 2005

(87) PCT Pub. No.: WO2004/017063

PCT Pub. Date: Feb. 26, 2004

(65) Prior Publication Data

US 2006/0125489 A1    Jun. 15, 2006

(30) Foreign Application Priority Data

Jul. 19, 2002 (DE) .................... 102 32 940
Feb. 28, 2003 (DE) .................... 103 08 975

(51) Int. Cl.
*G01R 27/04* (2006.01)
*G01N 33/20* (2006.01)
*G01N 11/16* (2006.01)

(52) U.S. Cl. .................... 324/633; 73/61.43; 73/54.41

(58) Field of Classification Search ................ 324/633; 73/54.24
See application file for complete search history.

(56) References Cited

U.S. PATENT DOCUMENTS 4,783,987 A * 11/1988 Hager et al. ................ 73/32 A (Continued)

FOREIGN PATENT DOCUMENTS

EP      1 054 460      11/2000

(Continued)

OTHER PUBLICATIONS

R.M. White: "Surface acoustic wave sensors" Ultrasonics Symposium 1985, 1985, p. 490-494, XP001155517 the whole document.

(Continued)

*Primary Examiner*—Diego Gutierrez
*Assistant Examiner*—Jeff Natalini
(74) *Attorney, Agent, or Firm*—Young & Thompson (57) ABSTRACT

A device for detecting at least one substance of a fluid includes at least one piezo-acoustic resonator with at least one piezo layer, an electrode arranged on the piezo-electric layer, at least one other electrode arranged on the piezo-electric layer and a surface section used for sorption of the substance of the fluid. The piezo-electric layer, the electrodes and the surface section are disposed in such a way that electric control of the electrodes leads to an oscillation of the resonator at a resonance frequency which depends upon the amount of the substance which is sorbed on the surface section. The thickness of the pioelectric layer is in the region of 0.5 to 20 μm and the resonance frequency of the oscillation ranges from 500 MHz to 2 GHz. The device is a mass sensor with a piezo-acoustic high-frequency thin film resonator.

22 Claims, 6 Drawing Sheets

U.S. PATENT DOCUMENTS

| | | | | |
|---|---|---|---|---|
| 4,870,313 | A | * | 9/1989 | Hirama et al. ............... 310/320 |
| 5,075,641 | A | | 12/1991 | Weber et al. ............ 331/108 C |
| 5,130,257 | A | * | 7/1992 | Baer et al. .................. 436/151 |
| 5,747,857 | A | * | 5/1998 | Eda et al. ..................... 257/416 |
| 5,932,953 | A | | 8/1999 | Drees et al. ................. 310/324 |
| 5,936,150 | A | * | 8/1999 | Kobrin et al. ............... 73/24.06 |
| 6,607,934 | B2 | * | 8/2003 | Chang et al. .................. 438/50 |
| 6,684,683 | B2 | * | 2/2004 | Potyrailo et al. ........... 73/24.06 |
| 2004/0256961 | A1 | * | 12/2004 | Namba et al. ............... 310/365 |

FOREIGN PATENT DOCUMENTS

| | | |
|---|---|---|
| EP | 1 143 241 | 10/2001 |
| JP | 10-261934 | 9/1998 |

OTHER PUBLICATIONS

Ferrari V et al: "Multisensor array of mass microbalances for chemical detection based on resonant piezo-layers of screen-printed PZT" Sensors and Actuators B, Elsevier Sequoia S.A., Lausanne, CH, vol. 68, No. 1-3, Aug. 25, 2000, pp. 81-87, XP004216596 ISSN: 0925-4005 cited in the application the whole document.

I. Willner, E. Katz: "Redoxproteinschichten auf leitenden Tragern—Systeme fur bioelektronische Anwendungen" Angew. Chem., vol. 112, 2000, pp. 1230-1269, XP002269190 cited in the application the whole document.

Liang Hongwei et al: "Material parameter characterization of multilayer LTCC and implementation of high Q resonators" IEEE MTT S Int Microwave Symp Dig; IEEE MTT-S International Microwave Symposium Digest 1999 IEEE, Piscataway, NJ, USA, vol. 4, 1999, pp. 1901-1904, XP0010343609 the whole document.

C. Koblinger et al., Biosensors & Bioelectronics, 7 (1992), S. 397 bis 404.

G. Sauerbrey, Zeitschrift fur Physik, 155 (1959), S. 206-222.

H. Baltes, Proceedings of the IEEE, vol. 86, No. 8, Aug. 1998, Seiten 1660-1678.

* cited by examiner

| Bringing together the fluids with the substance and the surface section for sorption of the substance | 61 |

| Determination of the resonance frequency of the resonator | 62 |

DEVICE AND METHOD FOR DETECTING A SUBSTANCE OF A LIQUID

CROSS REFERENCE TO RELATED APPLICATION

This is the 35 USC 371 national stage of international application PCT/DE03/02226 filed on Jul. 3, 2003, which designated the United States of America.

FIELD OF THE INVENTION

The invention relates to a device for detecting at least one substance of a fluid, said device comprising at least one piezo acoustic resonator with at least one piezoelectric layer, an electrode disposed on the piezoelectric layer, at least one further electrode disposed on the piezoelectric layer, and a surface section used for sorption of the substance of the fluid, whereby the piezoelectric layer, the electrodes and the surface section are arranged in relation to one another in such a way that electrical actuation of the electrodes leads to an oscillation of the resonator at a resonance frequency and the resonance frequency is dependent on the amount of the substance which is adsorbed on the surface section. In addition a method for detecting at least one substance of a fluid using said device is specified.

BACKGROUND OF THE INVENTION

Biosensors are used to an increasing extent in modern biological analysis technology and in medical diagnostics. A biosensor consists of a biological detection system for a biological substance and what is referred to as a physical transducer. The substance is "detected" via the biological detection system. Said "detection" is converted into an electronic signal by means of the physical transducer. Frequently used biological detection systems are antibodies, enzymes and nucleic acids. In this case the biological detection systems are usually immobilized (fixed) on the transducer in approximately two-dimensional layers. An immobilization (fixing) can be effected in this case by covalent bindings, by affinity interactions and by hydrophilic or hydrophobic interactions. An overview of a structure consisting of approximately two-dimensional biological detection layers is given by I. Willner and E. Katz in Angew. Chem. ("Applied Chemistry") 112 (2000), 1230 to 1269.

A device and a method of the type cited at the beginning are known from C. Kösslinger et al., Biosensors & Bioelectronics, 7 (1992), pp. 397 to 404. The surface section of the resonator constitutes a detection system for a substance. The piezoelectric resonator acts as a physical transducer. The piezoelectric layer of the known resonator consists of a quartz crystal. Gold electrodes are attached to the quartz crystal. The quartz crystal is excited by electrical actuation of the electrodes to produce bulk acoustic waves in the form of thickness shear mode oscillations. The resonance frequency is about 20 MHz. One of the electrodes forms the surface section used for sorption of the substance of the fluid. The substance is a macromolecular protein which is present in a liquid and which is physically adsorbed at the electrode. As a result of the adsorption of the protein there is a change in the mass and therefore the resonance frequency of the resonator. The following general relationship applies to the change in the resonance frequency ($\Delta f$) as a function of the change in the adsorbed amount of the substance per surface unit ($\Delta m$) (cf. G. Sauerbrey, Zeitschrift für Physik ("Journal for Physics"), 155 (1959), pp. 206-222):

$$S = \frac{\Delta f}{\Delta m} = c \frac{f_0}{m} \propto f_0^2 \qquad (1)$$

where S is the mass sensitivity of the resonator, $f_0$ is the resonance frequency of the resonator without adsorbed substance, c is a material-specific constant, and m is the mass of the resonator per surface unit. The mass sensitivity is proportional to the square of the resonance frequency of the resonator. At a relatively low resonance frequency $f_0$ of approx. 20 MHz the mass sensitivity of the known device can be estimated at approx. 1 Hz·ng$^{-1}$·cm$^2$.

A device and a method of the cited type are also known from V. Ferrari et al., Sensors and Actuators, B 68 (2000), pp. 81-87. The device operates as a mass sensor used for detection of a chemical substance. The piezoelectric layer is a plumbum zirconate titanate (PZT) layer. Layer-shaped electrodes (electrode layers) made of a silver-palladium alloy are applied on opposite sides of the PZT layer. The electrodes and the PZT layer form the piezo acoustic resonator. The resonator can be excited to generate a longitudinal oscillation along the layer thickness of the PZT layer by electrical actuation of the electrodes.

The known resonator has a surface section on which a substance can be sorbed. Toward that end the resonator has a chemically sensitive coating forming the surface section. The chemically sensitive coating is a polymer film which is applied to one of the electrodes. The polymer film is for example polystyrole or polymethylacrylate. Various substances, for example hydrocarbons, can be adsorbed on these polymer films. The adsorption causes a change in the mass of the resonator. As a result of this the resonance frequency of the resonator changes. The extent of the change in the resonance frequency is dependent on the adsorbed amount of the substance. The more substance is adsorbed, the greater is the change in the resonance frequency.

The layer thickness of the PZT layer of the resonator is approximately 100 μm. The electrodes are approx. 10 μm thick. The polymer film is applied for example at a thickness of approx. 3 μm. A lateral extension of the resonator is approx. 6 mm. The resonance frequency of the resonator is approximately 7 MHz. The known device having the piezo acoustic resonator is suitable for the detection of a substance of a fluid. The fluid is either a liquid or a gas or gas mixture.

The resonator of the device is mounted on an aluminum oxide substrate. Thick-film technology (TFT) is the method chosen for manufacturing the resonator or, as the case may be, for attaching the resonator to the substrate. Miniaturization of the device is limited due to the resolution that can be achieved using thick-film technology. Increasing miniaturization is desirable, however. For example, a plurality of resonators are combined to form a resonator array. Each of the resonators forms an array element of the resonator array. The smallest possible resonator elements are required in order to be able to arrange the maximum number of array elements on a substrate of a given size.

In addition to the unfavorable size of the resonator from the point of view of miniaturization, the known device is characterized by a relatively low mass sensitivity (cf. Equation 1) due to the relatively low resonance frequency of the resonator. A low concentration of the substance of the fluid or a slight change in the concentration of the substance in the fluid can only be determined with a relatively large error margin.

A so-called "flexural plate wave" (FPW) sensor is known from H. Baltes, Proceedings of the IEEE, Vol. 86, No. 8, August 1998, pages 1660-1678. The sensor is a device for detecting a substance. The device has a piezo acoustic resonator which is mounted on a semiconductor substrate made of silicon. Vapor deposition methods, CMOS (Complementary Metal Oxide Semiconductor) technology and frontside or backside etching of the semiconductor substrate (bulk micromachining) are used in the fabrication of the device. The electrodes and the piezoelectric layer are arranged on the semiconductor substrate in the form of what is called a "cantilever" in such a way that electrical actuation of the electrodes leads to a lateral oscillation of the resonator at a resonance frequency of approx. 140 kHz. The resonator has a chemically sensitive coating made of polyurethane or polysiloxane. These polymers are suitable for the adsorption and therefore for demonstrating the presence of hydrocarbons containing halogens. The fluid is in particular gaseous. If the fluid is channeled past the surface section formed by one of the polymers, the hydrocarbons are adsorbed on the surface section. The mass of the resonator, and therefore also the resonance frequency of the resonator, changes as a function of the concentration of the hydrocarbons. The lateral extension of the resonator is relatively small. It amounts, for example, to 300 μm. However, the resonator is characterized by a relatively low mass sensitivity due to the relatively low resonance frequency of approx. 140 kHz.

SUMMARY OF THE INVENTION

The object of the present invention is to specify a substance-detecting device which has a higher mass sensitivity to the substance compared to the known prior art.

In order to achieve said object, a device for detecting at least one substance of a fluid is specified. The device has at least one piezo acoustic resonator comprising at least one piezoelectric layer, an electrode disposed on the piezoelectric layer, at least one further electrode disposed on the piezoelectric layer, and a surface section serving for sorption of the substance of the fluid, whereby the piezoelectric layer, the electrodes and the surface section are arranged in relation to one another in such a way that electrical actuation of the electrodes leads to an oscillation of the resonator at a resonance frequency and the resonance frequency is dependent on the amount of the substance which is sorbed on the surface section. The device is characterized in that a layer thickness of the piezoelectric layer is chosen from the range of 0.1 μm inclusive to 20 μm inclusive and the resonance frequency of the oscillation is chosen from the range of 500 MHz inclusive to 10 GHz inclusive.

The resonator of the device is a piezo acoustic thin-film resonator. The electrodes are formed from electrode layers.

The electrode layers consist, for example, of gold, aluminum or platinum. An overall layer thickness of the resonator comprising electrode layers and piezoelectric layer amounts, for example, to 1 μm. The mass of the resonator is reduced by comparison with the prior art owing to the small layer thickness of the piezoelectric layer or, as the case may be, by the small overall layer thickness. This increases the resonance frequency of the resonator. The high resonance frequency, which is also referred to as high frequency, results in a high mass sensitivity in relation to the substance. According to Equation (1), the mass sensitivity of the device can be estimated to a few $Hz \cdot pg^{-1} \cdot cm^2$. For example, the mass sensitivity at a resonance frequency of 1 GHz is equivalent to approx. 2.5 $Hz \cdot pg^{-1} \cdot cm^2$. A mass sensitivity improved by a factor of $10^3$ is achieved by means of the invention.

Sorption is understood to mean the formation of a chemical or physical bonding (binding) of the substance to the surface section. In this context sorption includes both absorption and adsorption. With absorption, the substance is absorbed for example through a resonator coating which forms the surface section, without formation of a phase boundary. The substance is incorporated into the coating. With adsorption, in contrast, a phase boundary is formed. Conceivable in particular in this case is an adsorption in the form of a physisorption (physical adsorption). The substance is deposited on the surface section of the resonator through van der Waals or dipole-dipole interactions. Alternatively, adsorption in the form of a chemisorption (chemical adsorption) can take place. With chemisorption, the substance is deposited on the surface section with formation of a chemical bond. The chemical bond is for example a covalent binding or a hydrogen bridge binding.

It is preferable if the sorption takes place as a reversible process. This means that the substance can also be subsequently desorbed (removed) from the surface section. For example the substance is removed again by increasing the temperature of the surface section or by the action of a reactive agent. The reactive agent is for example an acid or an alkaline solution by means of which the bindings formed during the chemisorption are dissolved. This enables the device to be used a number of times. However, it is also possible that the sorption is irreversible, in which case the device is used only once as a single-use sensor.

Every conceivable chemical or biological compound may be suitable as the substance. Thus, the device can be used as a gas sensor for detecting a gas. The gas is a substance which has a specific vapor pressure. Substances of this kind are for example organic solvents. It is also conceivable that such a substance is an explosive or a component, a primary product or a reduction product of an explosive. The device can be used as an explosives detector. It is also conceivable that the device is embodied as a biosensor for detection of any desired biomolecule. The biomolecule is for example a DNA (deoxyribonucleic acid) sequence or a macromolecular protein.

The surface section is preferably embodied in such a way that a specific substance or substance class is sorbed selectively according to the key-lock principle and thus detected. In this way it is possible to enlist the aid of the device to detect a specific substance selectively from a mixture consisting of a plurality of substances. In this case the detection comprises both a qualitative and a quantitative determination of the substance. The absence or the presence of the substance in the fluid can be proven. The concentration of the substance in the fluid can also be determined. A change in the concentration of the substance over time can also be determined by differential detection of the substance. Thus, the device is also suitable for example for reaction monitoring of a chemical reaction in which the substance is involved.

In particular the chemically sensitive coating has molecules for detecting the substance. In order to detect a specific DNA sequence, such molecules are appropriate oligonucleotides (DNA oligos) consisting of multiple nucleotide units.

In this case the molecules serving to detect the substance can be directly coupled to a transducer surface. The transducer surface is a gold electrode of the resonator, for example. Molecules that have a thiol group are attached directly to the transducer surface by formation of a gold-sulfur binding.

In a special embodiment the chemically sensitive coating has an immobilization layer for combining the resonator and the molecules for detecting the substance. A transducer surface has NH or OH groups, for example. In this case the molecules for detecting the substance can be immobilized via alkoxysilane, cyanurchloride or carbodiimide. These compounds form the immobilization layer.

The immobilization layer can be directly coupled to the transducer surface. It is also possible that the immobilization layer is coupled indirectly to the transducer surface via an adhesion promoter layer.

Essentially, the immobilization layer can be two-dimensional. The immobilization layer is arranged as an ordered monomolecular or multimolecular layer along the transducer surface. In particular, however, the immobilization layer is three-dimensional. An immobilization array is present. For example, the immobilization layer has open pores in which the molecules for detecting the substance are arranged. A chemically sensitive coating having a large "reactive" surface is present. As a consequence thereof, a chemically sensitive coating having a three-dimensional immobilization layer is characterized by an increased mass sensitivity for detection of the substance. The three-dimensional immobilization layer can be generated for example by radical networking of monomers. The molecules serving to detect the substance can be bound to the interconnected monomers. It is also conceivable that the monomers already have the functional groups for detecting the substance before the network is implemented.

The oscillation of the resonator is selected in particular from the longitudinal oscillation group and/or thickness shear mode oscillation group. Which type of oscillation is excited depends, among other factors, on a symmetry group of the piezoelectric material, the orientation of the piezoelectric layer toward the surface and the arrangement of the electrodes. The piezoelectric layer consists, for example, of a <111>-oriented plumbum zirconate titanate. If an electric field is applied only in the z-direction along the layer thickness of the piezoelectric layer, this results primarily in a longitudinal oscillation along the layer thickness. With the arrangement described, on the other hand, the thickness shear mode oscillation can occur along the lateral extension of the piezoelectric layer. In order to effect this, however, the thickness shear mode oscillation requires a lateral component of the exciting electric field. The longitudinal oscillation is used in particular for analyzing a gaseous fluid. In the case of a liquid fluid the longitudinal oscillation is relatively strongly attenuated, resulting in a substantial reduction in the mass sensitivity. In order to investigate a liquid fluid using the longitudinal oscillation of the resonator, the fluid is therefore removed from the surface section or, as the case may be, from the resonator after the sorption. The measurement of the resonance frequency of the resonator takes place after the sorption in the absence of the fluid. In contrast, measurement of the thickness shear mode oscillation is suitable for direct investigation of a liquid fluid. The thickness shear mode oscillation is only attenuated to an imperceptible degree in a liquid. The measurement can be taken when the resonator comes in contact with the liquid.

In a special embodiment the resonator has a lateral extension which is chosen from the range from 50 µm inclusive to 1000 µm inclusive. Owing to the small lateral extension the resonator can be used to analyze a small sample volume of the fluid.

In a special embodiment the piezoelectric layer has a piezoelectric material which is chosen from the plumbum zirconate titanate, zinc oxide and/or aluminum nitride group. These materials are particularly suitable for a deposition of the materials from the gas phase on a substrate. The deposition takes place for example in a chemical vapor deposition (CVD) method or in a physical vapor deposition (PVD) method. Sputtering is an example of the physical vapor deposition method. By means of the vapor deposition methods the small layer thickness of the piezoelectric layer and also small layer thicknesses of the electrodes are accessible.

The resonator can be disposed on any desired substrate which exhibits a low loss in respect of high frequency signals. Said substrate has for example a sapphire as the dielectric. In particular a high frequency substrate is conceivable. The high frequency substrate is characterized in that a high frequency signal having high quality and therefore low loss is forwarded. Use is made in particular of an LTCC (Low Temperature Cofired Ceramics) substrate as a high frequency substrate. Because of the use of glass ceramics sintering at low temperature, electrically highly conductive materials such as metallic copper or silver can be integrated in the LTCC substrate.

The resonator is disposed in particular on a semiconductor substrate. In this case the semiconductor substrate has in particular a semiconductor material which is chosen from the silicon and/or gallium arsenide group. These semiconductor materials are suitable for the use of bipolar and CMOS technology. By means of these technologies a circuit, for example an evaluation circuit for determining the resonance frequency of the resonator, can be integrated in the semiconductor substrate. The result is a high integration density.

In a special embodiment of the device, at least one device for acoustic insulation of the resonator and of the semiconductor substrate is present. The resonator and the semiconductor substrate are acoustically insulated from each other. Said acoustic insulation of the resonator and of the semiconductor substrate ensures that the resonance frequency of the resonator is independent of the semiconductor substrate. This results in a relatively high mass sensitivity. The device serving for acoustic insulation is for example an acoustic mirror integrated in the substrate. The acoustic mirror is for example an acoustic Bragg reflector which consists of $\lambda/4$-thick layers of different acoustic impedance. Alternatively the device is formed by a cavity in the substrate which is covered by a membrane. The resonator is coupled to the semiconductor substrate via the membrane (indirectly). The membrane consists for example of an oxide and/or nitride. The membrane is for example a multi-layer membrane consisting of an oxide layer and a nitride layer. To provide acoustic insulation it is also possible that a backside of the semiconductor substrate facing away from the resonator has a recess, said recess preferably being produced by backside etching of the semiconductor substrate. The resonator is coupled to the semiconductor substrate for example on a nitride membrane which is detached due to the recess.

In a special embodiment the surface section used for sorption of the substance of the fluid is arranged at a recess of the semiconductor substrate. The recess, which can be embodied for example as a device serving for acoustic insulation of the resonator and of the semiconductor substrate, has the surface section used for sorption of the substance. In this arrangement the surface section can be formed by a chemically sensitive coating of the resonator which is arranged in the recess and is accessible to the fluid. It is also feasible that the surface section is formed at least partially by an electrode or by the piezoelectric layer of the resonator which is accessible to the fluid in the area of the recess.

In a further embodiment of the device at least one evaluation device is present for determining the resonance frequency of the resonator. The evaluation device comprises for example a high frequency circuit into which the resonator is integrated as a frequency-determining component. The high frequency circuit is for example a PLL (Phased Locked Loop) into whose control loop the resonator is connected via PIN diodes. The control signal of the PLL is a measure for the change in the resonance frequency of the resonator. The change in the resonance frequency enables the sorption of the substance on the surface section of the resonator to be deduced. In particular the evaluation device is an internal evaluation device disposed in the semiconductor substrate. The internal evaluation device can be integrated in the semiconductor substrate using bipolar or CMOS technology in the known fashion. Thanks to the possibility of integrating the evaluation device in the semiconductor substrate the device can operate as a module of a so-called "lab on a chip".

Alternatively the evaluation device is an external evaluation device disposed outside of the semiconductor substrate. The evaluation device is for example an evaluation chip embodied for evaluating the resonance frequency. The evaluation chip is for example additionally mounted on the semiconductor substrate and in electrical contact with the resonator.

In a further embodiment at least one device is present for establishing electrical contact between the resonator and the external evaluation device, said device being a high frequency substrate chosen from the FR4 substrate and/or LTCC substrate group. The external evaluation device is mounted for example on an LTCC substrate and electrically connected to the resonator by means of the LTCC substrate. FR4 is a known high frequency material. Substrates made of other high frequency materials such as GETEK or R04003 are also feasible.

In a special embodiment the resonator with semiconductor substrate and the high frequency substrate are connected to each other by means of a flip-chip technology. The flip-chip technology is particularly space-saving. Electrical bonds are implemented in a vertical direction by means of what are known as "solder bumps". The solder bumps are small protuberances, for example small balls or spherules, made of a solder which are disposed on the substrate surface. The solder bumps consist for example of a gold-nickel or gold-tin alloy. The solder bumps remove the need for space-consuming connecting wires (bonding wires). The space saving means that further advances can be made with regard to the miniaturization of the device. A particularly advantageous aspect thereof is that interference due to the influence of bonding wire inductances can be largely eliminated. In addition, unnecessarily long electrical lines on the semiconductor substrate are avoided . . . At frequencies in the GHz range in particular, lines on a semiconductor substrate are characterized by considerable internal losses. By employing flip-chip technology it is possible to dispense with such lines to a large extent. The device for detecting a substance is therefore characterized by a particularly high level of operating reliability and quality and as a consequence thereof also by a particularly high mass sensitivity.

The use of flip-chip technology is particularly advantageous with the embodiment of the device in which the surface section used for sorption of the substance is disposed in the recess of the semiconductor substrate. An etched backside of the semiconductor substrate containing the surface section is used for sorption of the substance of the fluid. The side containing the resonator facing away from the backside serves to establish electrical contact with the electrodes of the resonator. Electrical and mechanical contact between the electrodes of the resonator and a possibly present high frequency substrate is established via solder bumps.

The surface section for sorption of the substance can be formed by one of the electrodes of the resonator. In a special embodiment the surface section for sorption of the substance of the fluid is formed by a chemically sensitive coating of the resonator. A coating which can sorb a specific substance or also a specific substance class is applied to the resonator. The sorption is effected via chemisorption, physisorption or also absorption. The chemically sensitive coating is for example a polymer of the type cited at the beginning. It is also possible that the coating has a specific DNA sequence at the surface. The corresponding DNA sequence can dock with the said DNA sequence according to the key-lock principle. The corresponding DNA sequence is chemisorbed with formation of hydrogen bridge bindings. In this form the device is suitable for providing proof of a specific DNA sequence. A chemically sensitive coating for any chemical and biological substances is also possible.

However, the chemically sensitive coating can also be embodied to allow the adsorption of specific gaseous molecules. Molecules of this kind are for example carbon monoxide, carbon dioxide, nitric oxides or sulfur oxides. Low-molecular organic gases such as methane or ethane are also possible. The device is used for gas sensor applications.

In a special embodiment a plurality of resonators are combined to form a resonator array and each of the resonators forms an array element of the resonator array. Because of the small lateral extension of each individual resonator, considerably more resonators can be combined into a resonator array per surface unit compared to the prior art. In this case each of the resonators of the resonator array is preferably used for the detection of a specific substance. This means that each resonator is designed to be sensitive to a specific substance or substance class. In this way substance mixtures can be qualitatively and/or quantitatively analyzed with the aid of the device. In a gas sensor, for example, one of the resonators is sensitive to hydrocarbons, while a second resonator is sensitive to sulfur oxides and a further resonator is sensitive to carbon monoxide. In a biosensor, for example, each of the resonators of the individual array elements is sensitive to a specific DNA sequence. In this way it is possible to investigate the presence of different DNA sequences in the fluid in parallel.

The resonator array is embodied in particular on a semiconductor substrate. The resonator array is preferably produced on the semiconductor substrate using thin-film technology. In thin-film technology the individual resonators are manufactured in parallel in the same operating steps. As a result of the use of thin-film technology any variation in terms of the electrical properties of adjacent resonators is minor. If, for example, one resonator is provided with a chemically sensitive coating whereas an adjacent resonator is left uncoated, the change in the resonance frequency of the coated resonator compared to the resonance frequency of the uncoated resonator can be used for the purpose of detecting the substance. A differential measurement is possible.

A spacing between adjacent array elements is preferably chosen from the range of 20 µm inclusive to 1000 µm inclusive. This results in a device having a resonator array in which as many array elements as possible are integrated in as small a space as possible. Each of the array elements is very small.

Accordingly the result is a device with a very small total lateral extent.

According to a second aspect of the invention a method for detecting at least one substance of a fluid using the described device is specified. The method includes the method steps: bringing the fluid and the piezo acoustic resonator into contact with each other in such a way that the substance can be sorbed on the surface section of the resonator; and determination of a resonance frequency of the resonator, with the amount of the substance sorbed on the surface section being deduced from the resonance frequency. In order to be able to deduce the sorbed amount of the substance, the resonance frequency of the resonator without sorbed substance is usually determined before the fluid and the resonator are brought into contact.

The resonance frequency after the fluid and the resonator are brought into contact is preferably determined in the presence of the fluid. The fluid is for example a gas or gas mixture. The gas mixture is channeled past the surface section of one or more resonators. The substance is sorbed on the surface section. The sorption causes a change in the mass of the resonator and consequently in the resonance frequency of the resonator. The more substance is sorbed, the greater is the change in the resonance frequency compared to the resonator on whose surface section no substance is adsorbed.

According to a further embodiment the resonance frequency is determined in the absence of the fluid. For example, in a first step the fluid is channeled past the surface section of the resonator. The sorption takes place. Upon completion of the sorption the fluid ceases to be channeled past the surface section. The fluid is subsequently removed in such a way that the substance remains sorbed on the surface section of the resonator. Following this, the resonance frequency of the resonator is determined. This method is used in particular when a liquid is used as the fluid and the longitudinal oscillation of the resonator is used as the oscillation. As for the rest, it is also possible that the resonance frequency is determined both in the presence and in the absence of the fluid.

To sum up, the following advantages are produced by the invention:

- The device for detecting a substance is characterized by an improved mass sensitivity compared to the prior art. The mass sensitivity amounts to a few $Hz \cdot pg^{-1} \cdot cm^2$.
- The mass sensitivity can be additionally increased through the use of a three-dimensional immobilization array for molecules for detecting the substance.
- The high mass sensitivity means that the substance (analyte molecule) does not need to be marked for the purpose of detection. The detection process is "label-free".
- The resonator of the device is characterized by a small lateral extension. Because of the small lateral extension a plurality of resonators can be arranged on a substrate in a space-saving manner to form a resonator array. This results in a high integration density.
- The resonator array enables a plurality of substances to be detected in parallel.
- Because of the small lateral extension of the resonator a small specimen volume of the fluid can be examined.
- The device containing the resonator can be manufactured easily and at reasonable cost. Known thin-film technologies can be used for its manufacture. Through the use of a semiconductor substrate, CMOS technology and bulk micromachining processes can be used.
- A high frequency substrate in the form of an LTCC substrate is particularly suitable for electrical contacting of the resonator or resonators.
- The use of flip-chip technology largely eliminates high frequency losses and interfering inductances that can occur in bonding wires used for electrical contacting of the resonator. This results in a high operating reliability and quality and a high mass sensitivity. This applies in particular to a resonator array with a high density of array elements.

BRIEF DESCRIPTION OF THE DRAWINGS

The device and the method for detecting a substance of a fluid will now be presented with reference to a number of exemplary embodiments and the associated figures. The focus here will be on different individual aspects of the invention which can be combined with one another as desired. The figures are schematic and do not represent diagrams that are true to scale.

DETAILED DESCRIPTION OF THE INVENTION

The device 1 for detecting a substance consists of a piezo acoustic resonator 2 which is mounted on a semiconductor substrate 3 made of silicon. The resonator 2 has a piezoelectric layer 4 made of plumbum zirconate titanate. The plumbum zirconate titanate has a <111> orientation with respect to the semiconductor substrate 3. The layer thickness 7 of the piezoelectric layer 4 is approx. 0.8 µm. The lateral extension 11 of the resonator 2 is approx. 100 µm. In two alternative embodiments the piezoelectric layer consists of aluminum nitride and zinc oxide.

Figure 5A:
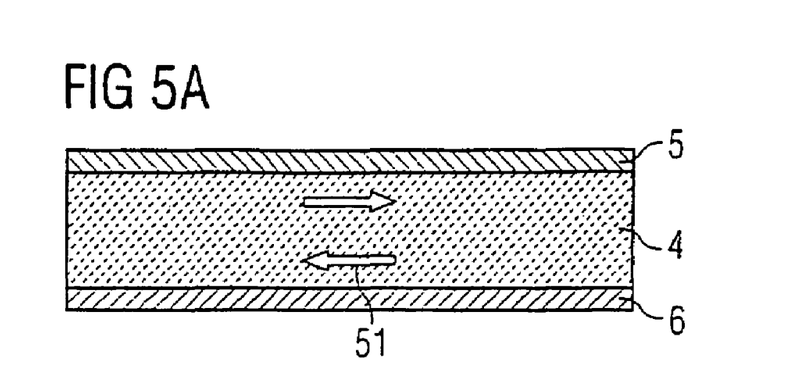
FIGS. 5a and 5b indicate different oscillation modes of the resonator.
Figure 5B:
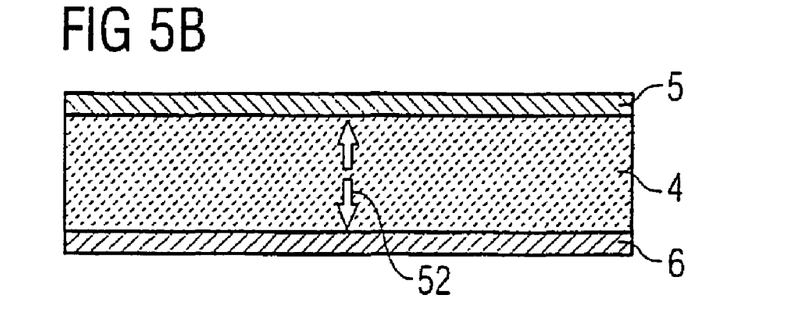

The layer thicknesses of the layer-shaped electrodes 5 and 6 disposed on the piezoelectric layer 4 are approx. 0.1 µm. The electrodes are made of gold. The resonator 2 is excited into an oscillation by electric actuation of the electrodes 5 and 6. The resonator 2 is excited into a thickness sheer mode oscillation 51 along a lateral extension 11 of the piezoelectric layer 4 (FIG. 5a) and/or into a longitudinal oscillation 52 along the layer thickness 7 of the piezoelectric layer 4 (FIG. 5b) as a function of the arrangement of the piezoelectric layer 4 and the electrodes 5 and 6 with respect to one another.

Figure 1A:
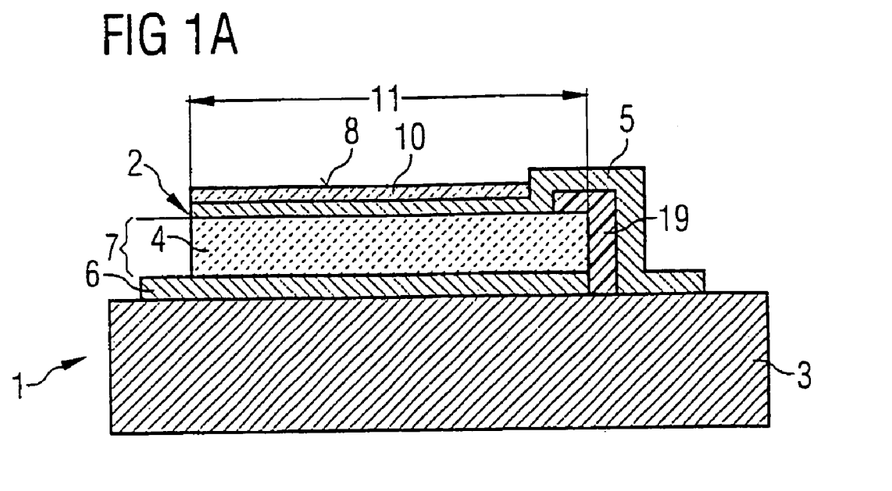
FIGS. 1a to 1f show, in cross-section, piezo acoustic resonators in which the electrodes, the piezoelectric layer and the surface section of the resonator are arranged differently with respect to one another.

According to FIG. 1a the electrodes 5 and 6 are disposed on two sides of the piezoelectric layer 4 which face away from each other. The electrodes 5 and 6 are additionally separated by an electrical insulation 19 made of aluminum oxide. The electrical actuation leads to a longitudinal oscillation 52 along the layer thickness 7 of the piezoelectric layer 4.

Figure 1B:
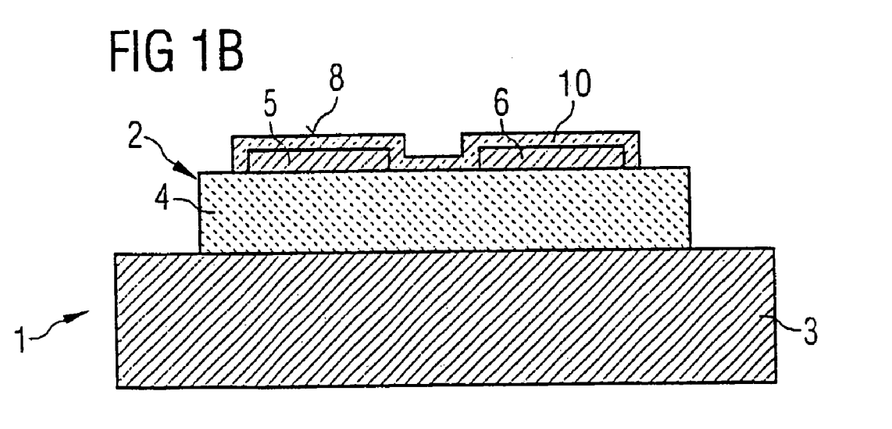

An arrangement according to FIG. 1b, in which the two electrodes 5 and 6 are disposed on one side of the piezoelectric layer 4, leads to a thickness shear mode oscillation 51.

Figure 1C:
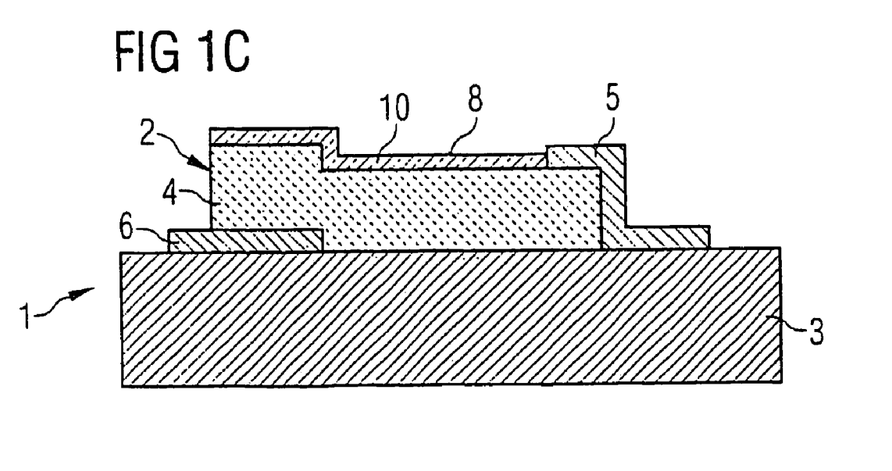

The arrangement according to FIG. 1c likewise leads to the development of a thickness shear mode oscillation 51.

Figure 1D:
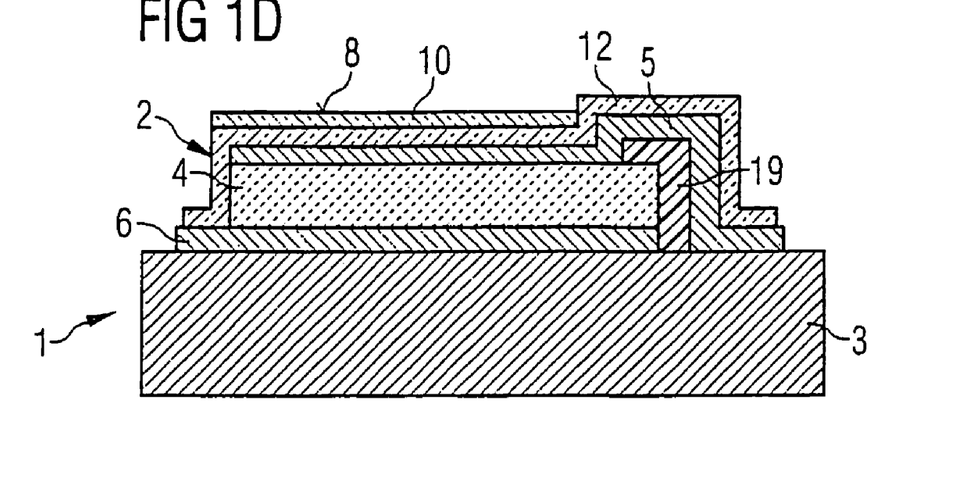

The resonator 2 has a surface section 8 on which a substance of a fluid 9 can be sorbed. For this purpose the resonator 2 has a chemically sensitive coating 10. The chemically sensitive coating 10 is applied to the electrode 5 (FIG. 1a). As an alternative to this, the chemically sensitive coating is applied to the two electrodes 5 and 6 (FIG. 1b). The chemically sensitive coating 10 can also be applied to the piezoelectric layer 4 (FIG. 1c). Alternatively, a protective layer 12 is applied to the resonator 4, onto which protective layer the chemically sensitive coating 10 is applied in turn (FIG. 1d). In an embodiment that is not shown the protective layer 12 itself acts a chemically sensitive coating 10.

Figure 1E:
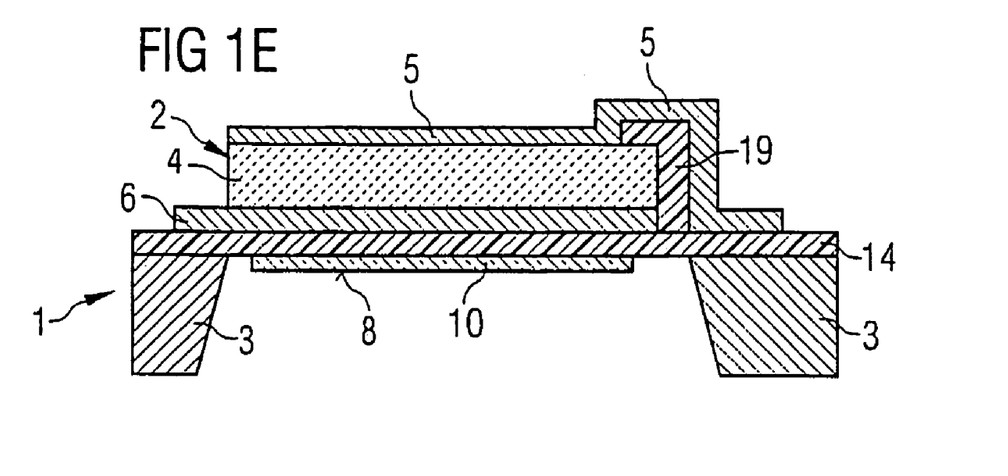

FIG. 1e shows a further alternative, according to which the chemically sensitive coating 10 is disposed in a recess 13 of the semiconductor substrate 3 on a membrane 14 made of a nitride. The recess 13 is produced by backside etching of the semiconductor substrate 3.

Figure 1F:
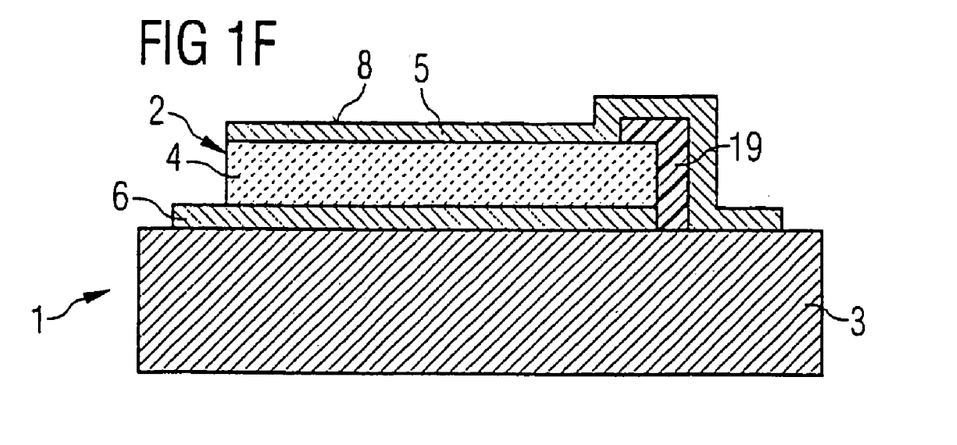

According to FIG. 1f, in contradistinction to the preceding examples, the electrode 5 forms the surface section 8 for sorption of the substance of the fluid 9. The substance is sorbed directly on the electrode.

Figure 2A:
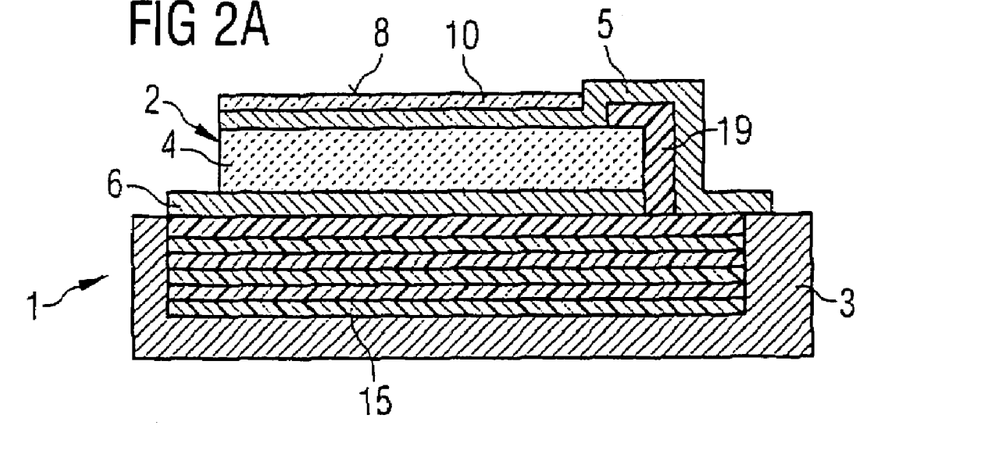
FIGS. 2a to 2c show different possibilities for acoustic insulation of a semiconductor substrate and the piezo acoustic resonator.
Figure 2B:
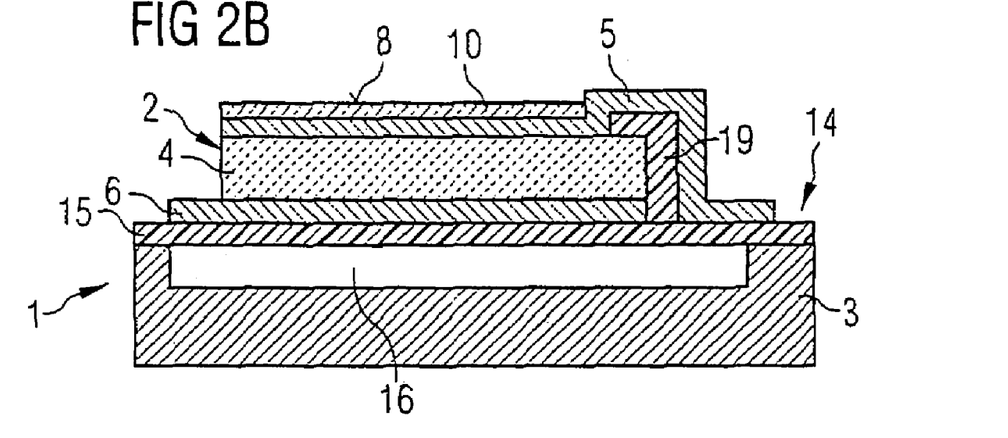

In order to increase the mass sensitivity of the resonator 2 to a specific substance, the semiconductor substrate 3 and the resonator 2 are acoustically insulated from each other by means of a device for acoustic insulation 15. According to FIG. 2a the device is a Bragg reflector with λ/4-thick layers of differing impedance. As an alternative thereto, a membrane 14 and a cavity 16 are integrated in the semiconductor substrate 3 underneath the resonator 2. The cavity 16 is covered by the membrane 14. The membrane 14 connects the resonator 2 and the semiconductor substrate 3. Membrane 14 and cavity 16 are implemented in the semiconductor substrate by means of bulk and/or surface micromachining.

Figure 2C:
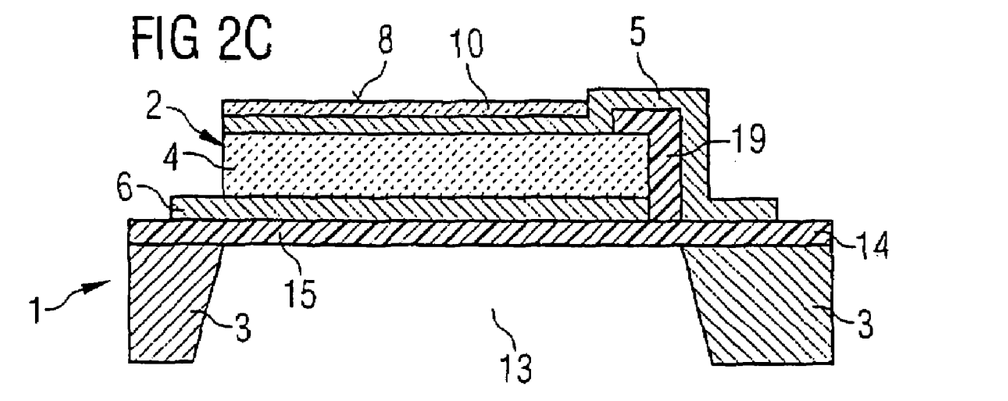

According to FIG. 2c the device 15 used for acoustic insulation is a recess 13 in the semiconductor substrate 3. Underneath the resonator 2 the material of the semiconductor substrate 3 is removed by backside etching. The resonator 2 is mounted on a membrane 14. The membrane 14 consists of a silicon nitride layer and a silicon oxide layer.

Figure 3A:
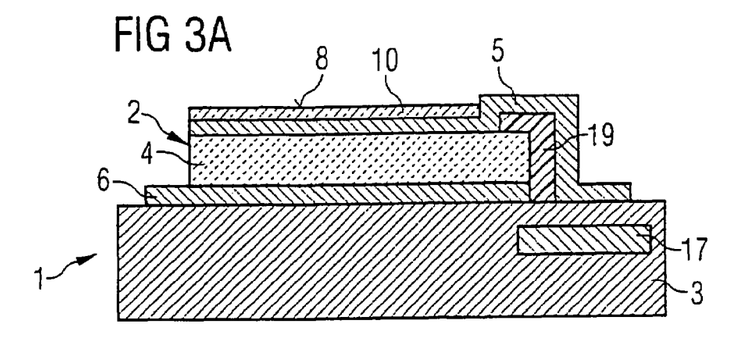
FIGS. 3a and 3b show devices with an internal and external evaluation device.

According to FIG. 3a an internal evaluation device 17 is present in the semiconductor substrate. The internal evaluation device 17 is integrated in the semiconductor substrate 3 by means of CMOS technology. The internal evaluation device 17 comprises a resonance circuit into which the resonator 2 is incorporated as a resonance-determining component.

Figure 3B:
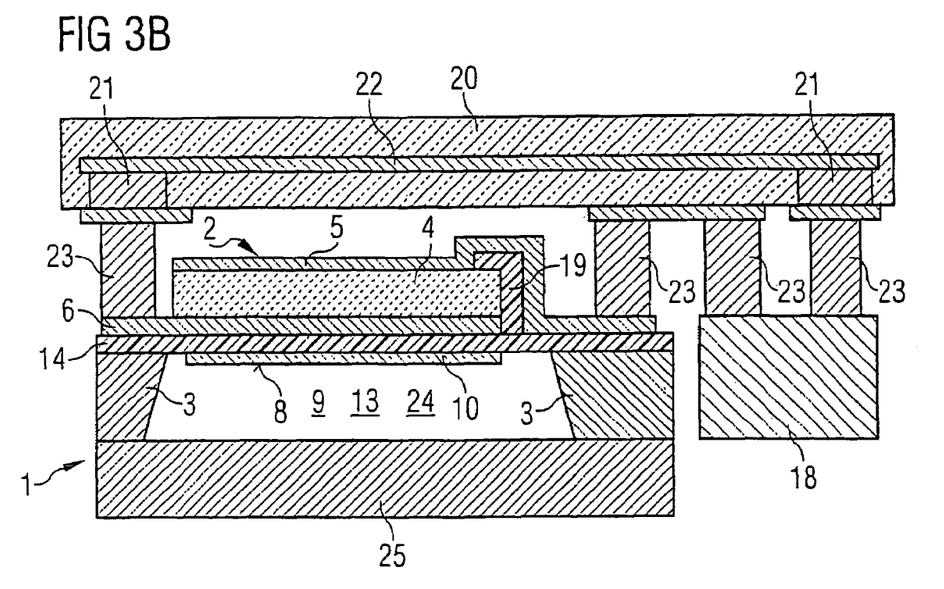

According to FIG. 3b the resonator 2 is connected to an external evaluation device 18. A high frequency substrate 20 in the form of an LTCC substrate is present for the purpose of establishing electrical contact between the resonator 2 and the evaluation device 18. Electrical interlayer connections 21 and electrical conductor tracks 22 made of silver are integrated in the LTCC substrate. Both the device 1 and the external evaluation device 18 are electrically contacted with the electrical interlayer connections 21 and conductor tracks 22 integrated in the LTCC substrate 20 via solder bumps 23 based on flip-chip technology. According to the embodiment shown in FIG. 3b the chemically sensitive coating 10 is disposed in the recess 13 of the semiconductor substrate 3. The recess 13 acts as a channel 24 through which the fluid 9 is supplied to the surface section 8 from a reservoir. The channel 24 is formed by the recess 13 of the semiconductor substrates and a cover 25 joined to the semiconductor substrate 3. The cover 25 is also made of silicon. In an alternative embodiment thereto the cover 25 is made of a plastic. The plastic and a possibly present seal between plastic and semiconductor substrate is passive with respect to the fluid 9. The fluid 9 can be routed through the channel 24 without causing a reaction to take place between a component of the fluid 9 and the plastic or a material of the seal.

Figure 4A:
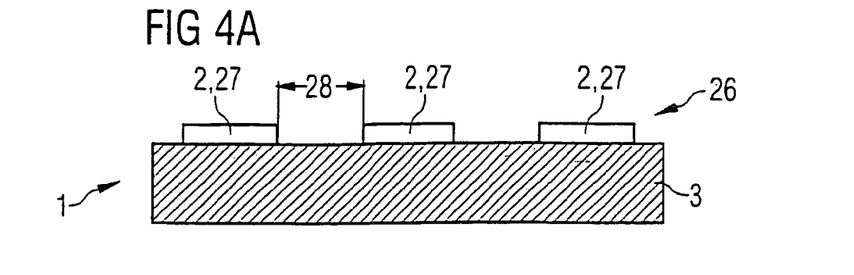
FIGS. 4a to 4c show a resonator array comprising a plurality of array elements in a cross-sectional view (FIG. 4a) and in a plan view (FIGS. 4b and 4c).
Figure 4B:
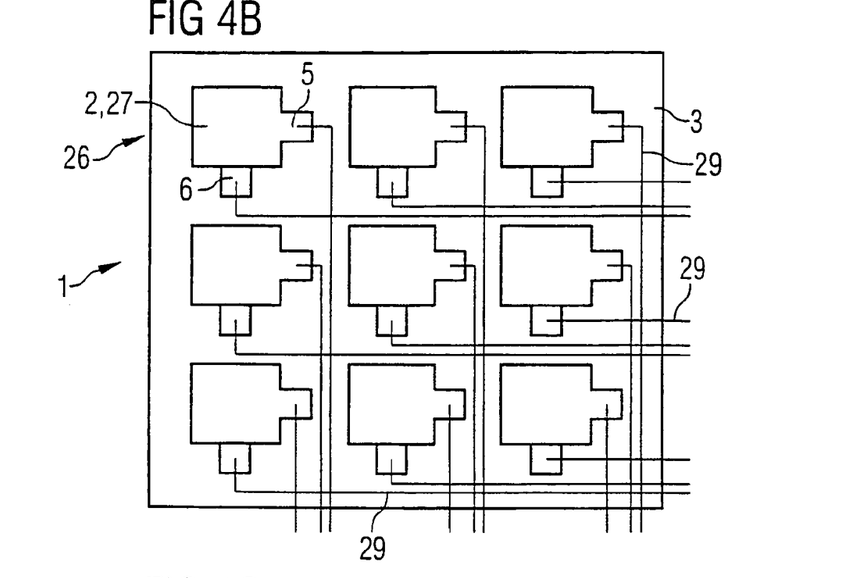
Figure 4C:
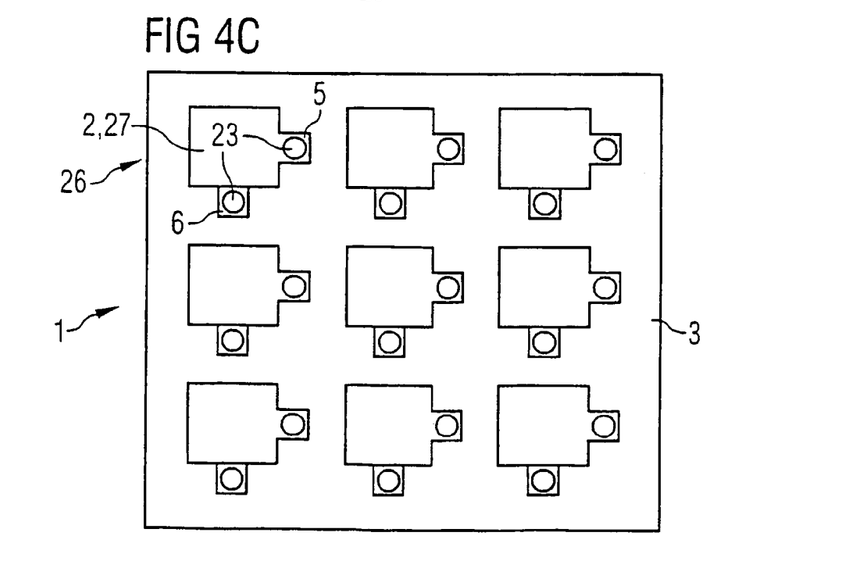

FIG. 4a shows a device 1 comprising three resonators 2 in a lateral cross-section along the connecting line I-I (see FIGS. 4b and 4c). The resonators 2 are mounted on a semiconductor substrate 3 made of silicon, forming a resonator array 26. Each of the resonators 2 forms an array element 27 of the resonator array 26. Each of the resonators 2 has a lateral extension 11 of approximately 100 μm. A spacing 28 between adjacent array elements 27 is 100 μm.

FIGS. 4b and 4c show different possibilities for establishing electrical contact between the individual array elements 26.

According to FIG. 4b the electrodes 5 and 6 of the resonators 2 of the individual array elements 27 are electrically contacted in the conventional way. Toward that end corresponding electrical lines 29 are present on the semiconductor substrate 3.

According to FIG. 4c the electrical contacting of the individual resonators 2 is realized via solder bumps 23 using flip-chip technology.

Each of the array elements 27 has a resonator 2 which is sensitive to a specific substance. This results in a device for detecting a plurality of substances of a fluid 9.

Figure 6:
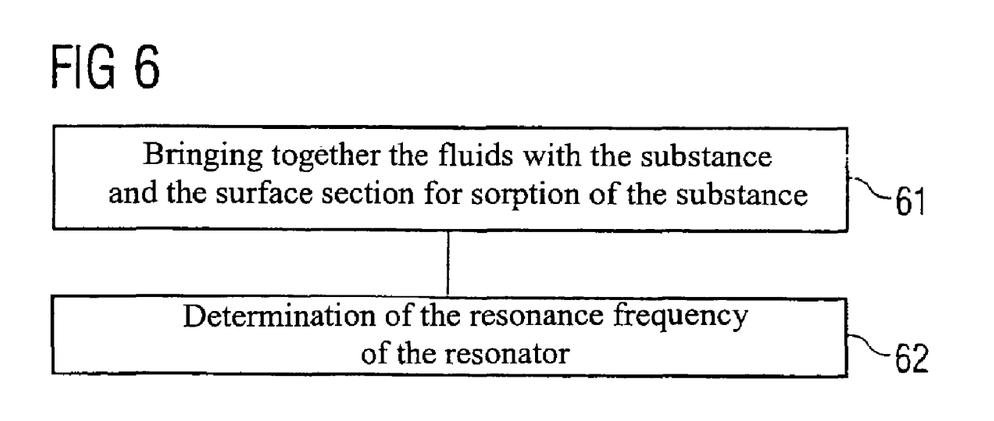
FIG. 6 shows a method for detecting a substance of a fluid.

In order to detect the substances contained in the fluid 9, in a first step in each case the surface section 3 of the resonator 3 and the fluid 9 are brought into contact (FIG. 6, step 61). Fluid 2 and resonator 2 are brought into contact in such a way that the substance of the fluid 9 can be sorbed on the respective surface sections 3 of the resonator 2. As a result of the sorption there is a change in the mass of the resonator 2. The type of the substance and its concentration in the fluid 9 can be deduced by subsequent measurement of the resonance frequencies of the resonator 2 (FIG. 6, step 62). As a result of the sorption of the substance there is a change in the resonance frequency of the resonator compared to the resonance frequency of the resonator on whose surface section no substance is sorbed. In order to be able to determine the change in the resonance frequency, a resonator with a known resonance frequency is used. In an alternative embodiment the resonance frequency of the resonator without sorbed substance is determined before the fluid and the resonator are brought into contact.

Protein Detection Example:

A chemically sensitive coating 10 formed from an oligonucleotide consisting of 25 bases is immobilized on the electrode 5 (made of gold) of the piezo acoustic resonator 2. The oligonucleotide is applied to the electrode 5 as a hydrous solution at a concentration of a few mmol in the sub-nanoliter range. Each of the oligonucleotides has a thiol-alkyl group at the 3' position and a biotin group at the 5' position. Sulfurgold bindings are formed via the thiol-alkyl group. The oligonucleotides are immobilized on the electrode 5. The basic oligonucleotide structure forms a kind of immobilization layer. The biotin group forms a strong complex with streptavidin. The biotin group acts in a way as a molecule for detecting the substance streptavidin. As soon as this protein is present in a fluid to which the described chemically sensitive coating 10 is exposed, the process of forming a complex is triggered, resulting in the sorption of the protein on the chemically sensitive coating 10.

DNA Detection Example:

Oligonucleotides consisting of 25 bases are immobilized via thiol-alkyl groups. The oligonucleotides have no biotin groups. DNA fragments containing a correspondingly complementary nucleotide sequence are bonded to the immobilized oligonucleotides through the formation of hydrogen bridge bindings.

The invention claimed is:

1. A device for detecting at least one substance of a liquid, having at least one piezo acoustic resonator comprising:
   at least one polycrystalline piezoelectric layer,
   an electrode disposed on the polycrystalline piezoelectric layer,
   at least one further electrode disposed on the polycrystalline piezoelectric layer, and
   a surface section for sorption of the substance of the liquid, wherein the polycrystalline piezoelectric layer, the electrodes and the surface section are arranged with respect to one another in such a way that an electrical actuation of the electrodes leads to an oscillation of the resonator at a resonance frequency and the resonance frequency is dependent on an amount of the substance sorbed on the surface section, a layer thickness of the polycrystalline piezoelectric layer is chosen from the range of 0.1 µm inclusive to 20 µm inclusive, the resonance frequency of the oscillation ranges from 500 MHz inclusive to 10 GHz inclusive and wherein the oscillation of the resonator is thickness shear mode oscillation.

2. The device as claimed in claim 1, wherein the resonator (2) has a lateral extension (11) which is chosen from the range of 20 µm inclusive to 1000 µm inclusive.

3. The device as claimed in claim 1, wherein the piezoelectric layer (4) has a piezoelectric material which is at least one member selected from the group consisting of plumbum zirconate titanate, zinc oxide and aluminum nitride.

4. The device as claimed in claim 1, wherein the resonator (2) is disposed on a semiconductor substrate (3).

5. The device as claimed in claim 4, wherein at least one device (15) is present to provide acoustic insulation of the resonator (2) and the semiconductor substrate (3).

6. The device as claimed in claim 4, wherein the surface section (8) for sorption of the substance of the liquid is disposed at a recess (13) of the semiconductor substrate (3).

7. The device as claimed in claim 1, wherein at least one evaluation device (17, 18) is present for determining the resonance frequency of the resonator (2).

8. The device as claimed in claim 7, wherein the evaluation device is an internal evaluation device (17) disposed in the semiconductor substrate (3).

9. The device as claimed in claim 7, wherein the evaluation device is an external evaluation device disposed outside of the semiconductor substrate (3).

10. The device as claimed in claim 9, wherein at least one device (20) is present for establishing electric contact between the resonator (2) and the external evaluation device (18), said device being a high frequency substrate which is at least one member selected from the group consisting of FR4 substrate and LTCC substrate.

11. The device as claimed in claim 10, wherein the resonator (2) with semiconductor substrate (3) and the high frequency substrate (20) are connected to each other by means of a flip-chip technology.

12. The device as claimed in claim 1, wherein the surface section (8) for sorption of the substance of the liquid (9) is formed by a chemically sensitive coating (10) of the resonator (2).

13. The device as claimed in claim 12, wherein the resonator (2) has a protective layer (12) and the chemically sensitive coating (10) is applied to the protective layer (12).

14. A device as claimed in claim 12, wherein the chemically sensitive coating has molecules for detecting the substance.

15. The device as claimed in claim 14, wherein the chemically sensitive coating has an immobilization layer for connecting the resonator and the molecules for detecting the substance.

16. The device as claimed in claim 1, wherein a plurality of resonators (2) are combined to form a resonator array (26) and each of the resonators (2) forms an array element (27) of the resonator array (26).

17. The device as claimed in claim 16, wherein each of the resonators (2) in the resonator array (26) serves to detect a specific substance.

18. The device as claimed in claim 16, wherein a spacing (28) between adjacent array elements (27) is chosen from the range of 50 µm inclusive to 1000 µm inclusive.

19. A method for detecting at least one substance of a liquid using a device according to claim 1, comprising the following method steps:
a) Bring the liquid and the piezo acoustic resonator into contact in such a way that the substance can be sorbed on the surface section of the resonator, and
b) Determine a resonance frequency of the resonator, whereby the amount of the substance sorbed on the surface section can be deduced from the resonance frequency.

20. The method as claimed in claim 19, wherein the resonance frequency is determined in the presence of the liquid.

21. The method as claimed in claim 19, wherein the resonance frequency is determined in the absence of the liquid.

22. The method as claimed in claim 21, wherein after the liquid and the resonator are brought into contact and before the resonance frequency is determined the liquid is removed in such a way that the substance remains sorbed on the surface section of the resonator.

* * * * *